(12) United States Patent
Turner et al.

(10) Patent No.: US 11,576,849 B2
(45) Date of Patent: Feb. 14, 2023

(54) ANTIMICROBIAL PERSONAL CLEANSING COMPOSITIONS

(71) Applicant: Conopco, Inc., Englewood Cliffs, NJ (US)

(72) Inventors: Graham Andrew Turner, Bromborough (GB); Christopher Francis Smith, Mansfield (GB)

(73) Assignee: CONOPCO, Inc., Englewood Cliffs, NJ (US)

( * ) Notice: Subject to any disclaimer, the term of this patent is extended or adjusted under 35 U.S.C. 154(b) by 280 days.

(21) Appl. No.: 16/497,680

(22) PCT Filed: Mar. 22, 2018

(86) PCT No.: PCT/EP2018/057379
§ 371 (c)(1),
(2) Date: Sep. 25, 2019

(87) PCT Pub. No.: WO2018/177903
PCT Pub. Date: Oct. 4, 2018

(65) Prior Publication Data
US 2021/0106513 A1 Apr. 15, 2021

(30) Foreign Application Priority Data

Mar. 30, 2017 (EP) .................................... 17163752

(51) Int. Cl.
| A61K 8/58 | (2006.01) |
| A61K 8/46 | (2006.01) |
| A61K 8/67 | (2006.01) |
| A61K 8/73 | (2006.01) |
| A61K 8/81 | (2006.01) |
| A61Q 5/02 | (2006.01) |

(52) U.S. Cl.
CPC .............. *A61K 8/58* (2013.01); *A61K 8/463* (2013.01); *A61K 8/675* (2013.01); *A61K 8/737* (2013.01); *A61K 8/8147* (2013.01); *A61Q 5/02* (2013.01)

(58) Field of Classification Search
CPC ....................................................... A61Q 5/02
See application file for complete search history.

(56) References Cited

U.S. PATENT DOCUMENTS

| 5,833,998 A * | 11/1998 | Biedermann .......... A61K 8/673 424/401 |
| 6,635,702 B1 * | 10/2003 | Schmucker-Castner ..................... A61K 8/891 524/291 |
| 2004/0234485 A1 | 11/2004 | Maubru et al. |
| 2008/0031842 A1 * | 2/2008 | Kuhlman ............. C11D 3/3765 424/70.11 |
| 2009/0169644 A1 * | 7/2009 | Goddinger ............ A61K 8/922 424/642 |
| 2014/0335041 A1 * | 11/2014 | Peffly .................... A61K 8/891 424/70.121 |
| 2015/0065476 A1 | 3/2015 | Aistrup et al. |

FOREIGN PATENT DOCUMENTS

| CN | 1530090 | 9/2004 |
| CN | 1778289 | 5/2006 |
| CN | 104822365 | 8/2015 |
| DE | 102006032505 | 1/2008 |
| EP | 2720666 | 3/2019 |
| KR | 20120051199 | 5/2012 |
| WO | WO2011101250 | 8/2011 |
| WO | WO2017042004 | 3/2017 |

OTHER PUBLICATIONS

Search Report and Written Opinion in EP17163752; dated Sep. 25, 2017.
Search Report and Written Opinion in PCTEP2018057379; dated Jun. 12, 2018.
Roberta del Sole et al.; Synthesis of nicotinamide-based molecularly imprinted microspheres and in vitro controlled release studies; Drug Delivery; Feb. 17, 2010; pp. 130-137; vol. 17, Issue 3; Informa Healthcare.

* cited by examiner

*Primary Examiner* — Gina C Justice
(74) *Attorney, Agent, or Firm* — Foley & Lardner LLP

(57) ABSTRACT

The invention provides an antimicrobial personal cleansing composition comprising: (i) an aqueous continuous phase including one or more anionic cleansing surfactants; (ii) a dispersed phase including dispersed particles of zinc pyrithione (ZPT); (iii) a structuring polymer for the aqueous continuous phase which is selected from crosslinked alkali-swellable acrylic emulsion (ASE) polymers; and (iv) from 3 to 20 wt % niacinamide based on the total weight of the composition, wherein the structuring polymer is selected from crosslinked copolymers of (meth)acrylic acid with one or more C1 to C5 alkyl esters of (meth)acrylic acid.

12 Claims, No Drawings

ANTIMICROBIAL PERSONAL CLEANSING COMPOSITIONS

The present application claims the benefit of priority under 35 U.S.C. 371 to International Application No. PCT/EP2018/057379, filed on Mar. 22, 2018, which in turn claims priority to European Application No. 17163752.3, filed Mar. 30, 2017, both of the contents of which are incorporated herein by reference in their entirety.

FIELD OF THE INVENTION

The present invention relates to antimicrobial personal cleansing compositions such as liquid soaps, body washes and shampoos.

BACKGROUND OF THE INVENTION

Zinc pyrithione (or ZPT) is an antimicrobial agent which is active against both gram-positive and gram-negative bacteria, as well as fungi and yeasts. It is widely used in antimicrobial personal cleansing compositions such as anti-dandruff (AD) shampoos. Generally, dispersed particles of the ZPT are suspended in the shampoo, which is then applied to the hair to deposit the ZPT particles on the hair and scalp.

Maximizing ZPT delivery during cleansing is a difficult task since most personal cleansing compositions were designed to carry away particulates from the skin or hair. Accordingly, efforts have been made to increase the antimicrobial efficacy of ZPT, for example by enhancing its distribution and bioavailability on the scalp.

The incorporation of niacinamide has been identified as a potential way to increase the antimicrobial efficacy of ZPT in the context of an AD shampoo However, the incorporation of niacinamide (especially at elevated levels) may impair product attributes such as viscosity and physical stability of the shampoo.

The present invention addresses this problem.

SUMMARY OF THE INVENTION

The invention provides an antimicrobial personal cleansing composition comprising:
(i) an aqueous continuous phase including one or more anionic cleansing surfactants;
(ii) a dispersed phase including dispersed particles of zinc pyrithione (ZPT);
(iii) a structuring polymer for the aqueous continuous phase which is selected from crosslinked alkali-swellable acrylic emulsion (ASE) polymers; and (iv) from 3 wt % to 20 wt % niacinamide based on the total weight of the composition,
wherein the structuring polymer is selected from crosslinked copolymers of (meth)acrylic acid with one or more C1 to C5 alkyl esters of (meth) acrylic acid.

DETAILED DESCRIPTION AND PREFERRED EMBODIMENTS

Niacinamide, also known as nicotinamide, is the water-soluble form of vitamin B3 and has the structure given below:

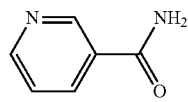

Herein, by 'soluble' is meant having a solubility of greater than 0.1 g/100 mL at 20° C. The level of niacinamide in compositions of the invention is suitably at least 3%, and preferably at least 5% by weight based on the total weight of the composition. In a typical composition according to the invention the level of niacinamide will generally range from 3 to 20% and preferably ranges from 5 to 15% by weight based on the total weight of the composition.

The composition according to the invention comprises an aqueous continuous phase (i) including one or more anionic cleansing surfactants.

By "aqueous continuous phase" is meant a continuous phase which has water as its basis. Suitably, the composition of the invention will comprise from 50 to 90%, preferably from 55 to 85%, more preferably from 60 to 85%, most preferably from 65 to 83% water (by weight based on the total weight of the composition).

Typical anionic cleansing surfactants for use in the invention include those surface active agents which contain an organic hydrophobic group with from 8 to 14 carbon atoms, preferably from 10 to 14 carbon atoms in their molecular structure; and at least one water-solubilising group which is preferably selected from sulphate, sulphonate, sarcosinate and isethionate.

Specific examples of such anionic cleansing surfactants include ammonium lauryl sulphate, ammonium laureth sulphate, trimethylamine lauryl sulphate, trimethylamine laureth sulphate, triethanolamine lauryl sulphate, trimethylethanolamine laureth sulphate, monoethanolamine lauryl sulphate, monoethanolamine laureth sulphate, diethanolamine lauryl sulphate, diethanolamine laureth sulphate, lauric monoglyceride sodium sulphate, sodium lauryl sulphate, sodium laureth sulphate, potassium lauryl sulphate, potassium laureth sulphate, sodium lauryl sarcosinate, sodium lauroyl sarcosinate, lauryl sarcosine, ammonium cocoyl sulphate, ammonium lauroyl sulphate, sodium cocoyl sulphate, sodium lauryl sulphate, potassium cocoyl sulphate, potassium lauryl sulphate, monoethanolamine cocoyl sulphate, monoethanolamine lauryl sulphate, sodium tridecyl benzene sulphonate, sodium dodecyl benzene sulphonate, sodium cocoyl isethionate and mixtures thereof.

A preferred class of anionic cleansing surfactants for use in the invention are alkyl ether sulphates of general formula:

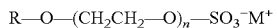

$$R-O-(CH_2CH_2-O)_n-SO_3^- M^+$$

in which R is a straight or branched chain alkyl group having 10 to 14 carbon atoms, n is a number that represents the average degree of ethoxylation and ranges from 1 to 5, preferably from 1 to 3, and M is a alkali metal, ammonium or alkanolammonium cation, preferably sodium, potassium, monoethanolammonium or triethanolammonium, or a mixture thereof.

Specific examples of such preferred anionic cleansing surfactants include the sodium, potassium, ammonium or ethanolamine salts of $C_{10}$ to $C_{12}$ alkyl sulphates and $C_{10}$ to $C_{12}$ alkyl ether sulphates (for example sodium lauryl ether sulphate), Mixtures of any of the above described materials may also be used.

In a typical composition according to the invention the level of anionic cleansing surfactant will generally range from 8 to 25%, and preferably ranges from 10 to 16% by weight based on the total weight of the composition.

In a preferred composition according to the invention the anionic cleansing surfactant is sodium lauryl ether sulphate having an average degree of ethoxylation of 1 (1EO), at a level of from 10 to 16% (by weight based on the total weight of the composition).

The aqueous continuous phase of the composition according to the invention preferably also includes one or more amphoteric surfactants, in addition to the anionic cleansing surfactant described above. Suitable amphoteric surfactants are betaines, such as those having the general formula $R(CH_3)_2N^+CH_2COO^-$, where R is an alkyl or alkylamidoalkyl group, the alkyl group preferably having 10 to 16 carbon atoms. Particularly suitable betaines are oleyl betaine, caprylamidopropyl betaine, lauramidopropyl betaine, isostearylamidopropyl betaine, and cocoamidopropyl betaine. Mixtures of any of the above described materials may also be suitable. Cocoamidopropyl betaine is particularly preferred.

When included, the total level of amphoteric surfactant is preferably from 0.1 to 10%, more preferably from 0.5 to 5%, and most preferably from 1 to 3% (by weight based on the total weight of the composition).

The antimicrobial personal cleansing composition according to the invention comprises a dispersed phase (ii) including dispersed particles of zinc pyrithione (ZPT).

Zinc pyrithione (ZPT) has the following chemical structure:

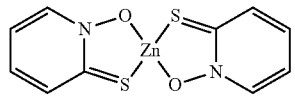

The ZPT particles may be amorphous, or may take various regular or irregular crystalline forms such as rods, needles, blocks, platelets and mixtures thereof. The average particle diameter of the ZPT particles (maximum dimension) is typically from 0.1 to 50 µm, preferably from 0.1 m to 10 µm, more preferably from 0.1 µm to 5 µm as determined, for example, using a Horiba LA-910 Laser scattering particle size distribution analyzer.

The level of ZPT in compositions of the invention generally ranges from 0.1 to 3%, and preferably ranges from 0.2 to 2%, more preferably from 0.5 to 1.5% (by weight based on the total weight of the composition).

Preferably, the composition of the invention further comprises one or more cationic polymers. Such polymers may enhance the delivery of conditioning agents and thereby improve the conditioning benefits obtained.

Cationic polymers for use in the invention suitably have a cationic charge density ranging from 0.3 to 4 meq/g, preferably from 0.4 to 3.5 meq/g. The term "cationic charge density" in the context of this invention refers to the ratio of the number of positive charges on a monomeric unit of which a polymer is comprised to the molecular weight of the monomeric unit. The charge density multiplied by the polymer molecular weight determines the number of positively charged sites on a given polymer chain. Cationic charge density can be determined according to the Kjeldahl Method. Those skilled in the art will recognize that the charge density of amino-containing polymers may vary depending upon pH and the isoelectric point of the amino groups. The charge density should be within the above limits at the pH of intended use.

Suitable cationic polymers for use in the invention include cationic polysaccharide derivatives, such as cationic cellulose derivatives, cationic starch derivatives, and cationic guar gum derivatives.

Preferred cationic polysaccharide derivatives for use in the invention include cationic guar gum derivatives and cationic cellulose derivatives.

Examples of preferred cationic guar gum derivatives for use in the invention include guar hydroxypropyltrimethylammonium chlorides. Guar hydroxypropyltrimethylammonium chlorides for use in the invention are generally comprised of a nonionic guar gum backbone that is functionalized with ether-linked 2-hydroxypropyltrimethylammonium chloride groups, and are typically prepared by the reaction of guar gum with N-(3-chloro-2-hydroxypropyl) trimethylammonium chloride.

Guar hydroxypropyltrimethylammonium chlorides for use in the invention generally have an average molecular weight (weight average molecular mass (Mw) determined by size exclusion chromatography) in the range 500,000 to 3 million g/mol, more preferably 800,000 to 2.5 million g/mol.

Guar hydroxypropyltrimethylammonium chlorides for use in the invention generally have a charge density ranging from 0.5 to 1.8 meq/g.

Examples of preferred cationic cellulose derivatives for use in the invention include poly(1,2-oxyethanediyl)-2-hydroxy-3-trimethylammonium propyl chloride cellulose ethers (INCI: Polyquaternium-10).

Mixtures of any of the above described cationic polymers may also be used.

In a typical composition according to the invention the amount of cationic polymer will generally range from 0.05 to 0.5%, and preferably ranges from 0.15 to 0.2% by weight based on the total weight of the composition.

In a preferred composition according to the invention the one or more cationic polymers are selected from guar hydroxypropyltrimethylammonium chlorides having a Mw ranging from 800,000 to 2.5 million g/mol and a charge density ranging from 0.5 to 1.8 meq/g; in an amount ranging from 0.15 to 0.2% (by weight based on the total weight of the composition).

The composition of the invention comprises a structuring polymer (iii) for the aqueous continuous phase which is selected from crosslinked alkali-swellable acrylic emulsion polymers.

Alkali-swellable acrylic emulsion polymers (ASE polymers) are carboxyl-containing copolymers that are prepared by the addition polymerization of ethylenically unsaturated monomers. The polymers are insoluble in water at low pH, but exhibit chain expansion and concomitant dissolution at pH greater than 6 upon neutralization with a base.

Exemplary ASE polymers for use as the structuring polymer (iii) in the invention may be prepared by the addition polymerization of a monomer mixture including at least one unsaturated carboxylic acid containing monomer, such as methacrylic acid or acrylic acid, and at least one nonionic vinyl monomer, such as alkyl acrylate or alkyl methacrylate.

Preferred ASE polymers for use as the structuring polymer (iii) in the invention may be prepared by the addition polymerization of a monomer mixture comprising three polymerizable monomeric components.

The first monomeric component is selected from one or more unsaturated carboxylic acid containing monomers having a total of from 3 to 10 carbon atoms atoms and preferably from 3 to 5 carbon atoms. Examples of such monomers include α-β-unsaturated monocarboxylic acids such as acrylic acid, methacrylic acid, and crotonic acid; or dicarboxylic acids such as itaconic acid, fumaric acid, maleic acid and aconitic acid. Half ester monomers of the dicarboxylic acids with C1 to C4 alkanols may also be used, such as monomethyl fumarate. Also, the dicarboxylic acids capable of forming cyclic anhydrides, such as maleic acid, may be polymerized as the anhydride and later reacted with water.

Preferably the unsaturated carboxylic acid containing monomers are selected from acrylic acid, methacrylic acid and mixtures thereof.

The amount of the unsaturated carboxylic acid containing monomers is preferably from 20 to 80%, more preferably from 25 to 70%, and most preferably from 35 to 65% by weight based on the total weight of all the monomers making up the ASE polymer.

The second monomeric component is selected from one or more nonionic vinyl monomers, typically (meth) acrylate or hydroxy (meth) acrylate esters in which the ester portion has from 1 to 10 carbon atoms. Examples of such monomers include methyl (meth) acrylate, ethyl (meth) acrylate, n-butyl (meth) acrylate, 2-ethylhexyl (meth) acrylate and 2-hydroxyethyl(meth)acrylate and mixtures thereof.

As used herein, the term "(meth)acrylate" denotes acrylate and/or methacrylate.

Preferably the nonionic vinyl monomers are selected from C1 to C5 alkyl (meth) acrylates and mixtures thereof. More preferably the nonionic vinyl monomers are selected from methyl acrylate, ethyl acrylate, butyl acrylate and mixtures thereof.

The amount of nonionic vinyl monomers is preferably from 80 to 15%, more preferably from 75 to 25%, and most preferably from 65 to 35% by weight based on the total weight of all the monomers making up the ASE polymer.

The third monomeric component is selected from one or more polyunsaturated crosslinking monomers. The polyunsaturated crosslinking monomer is utilized to generate either a partially or substantially-crosslinked three-dimensional polymeric network. By "polyunsaturated" is meant that the crosslinking monomer contains at least two polymerizable double bonds that are reactive with the first and second monomeric components as described above. Examples of suitable polyunsaturated crosslinking monomers include: di(meth)acrylate compounds such as ethylene glycol di(meth)acrylate, polyethylene glycol di(meth)acrylate, triethylene glycol di(meth)acrylate, 1,3-butylene glycol di(meth) acrylate, 1,6-butylene glycol di(meth)acrylate, 1,6-hexanediol di(meth)acrylate, neopentyl glycol di(meth) acrylate, 1,9-nonanediol di(meth)acrylate, 2,2'-bis(4-(acryloxy-propyloxyphenyl)propane, and 2,2'-bis(4-(acryloxydiethoxy-phenyl)propane; tri(meth)acrylate compounds such as trimethylolpropane tri(meth)acrylate, trimethylolethane tri(meth)acrylate, and tetramethylolmethane tri(meth)acrylate; tetra(meth)acrylate compounds such as ditrimethylolpropane tetra(meth)acrylate, tetramethylolmethane tetra(meth)acrylate, and pentaerythritol tetra(meth) acrylate; hexa(meth)acrylate compounds such as dipentaerythritol hexa(meth)acrylate; allyl compounds such as allyl (meth)acrylate, diallylphthalate, diallyl itaconate, diallyl fumarate, and diallyl maleate; polyallyl ethers of sucrose having from 2 to 8 allyl groups per molecule; polyallyl ethers of pentaerythritol such as pentaerythritol diallyl ether, pentaerythritol triallyl ether, and pentaerythritol tetraallyl ether; and polyallyl ethers of trimethylolpropane such as trimethylolpropane diallyl ether and trimethylolpropane triallyl ether. Other suitable polyunsaturated crosslinking monomers include divinyl glycol, divinyl benzene, and methylenebisacrylamide. Mixtures of any of the above described polyunsaturated crosslinking monomers may also be used.

Preferably the polyunsaturated crosslinking monomers are selected from divinyl glycol, allyl ether of sucrose, allyl ether of pentaerythritol, diallylphthalate, and mixtures thereof.

The amount of the polyunsaturated crosslinking monomer is preferably from 0.01 to 5%, more preferably from 0.03 to 3%, and most preferably from 0.05 to 1% by weight based on the total weight of all the monomers making up the ASE polymer.

Preferred ASE polymers for use as the structuring polymer (iii) in the invention are generally free of any groups derived from associative monomers. "Associative" monomers may be generally characterised as having a polymerizable end group, a hydrophilic midsection and a hydrophobic end group (typically linear or branched alkyl having from 8 to 40 carbon atoms. The term "generally free" in the context of this invention denotes a content of less than 1%, preferably less than 0.5% and more preferably less than 0.2% by weight based on the total weight of all the monomers making up the ASE polymer.

Examples of preferred ASE polymers for use as the structuring polymer (iii) in the invention include crosslinked copolymers of (meth) acrylic acid with one or more C1 to C5 alkyl esters of (meth) acrylic acid.

In a typical composition according to the invention the amount of structuring polymer (iii) will generally range from 0.05 to 2%, preferably from 0.1 to 1.5%, more preferably from 0.1 to 1%, even more preferably from 0.5 to 1% by weight based on the total weight of the composition.

In a preferred composition according to the invention the structuring polymer (iii) is selected from crosslinked copolymers of (meth) acrylic acid with one or more C1 to C5 alkyl esters of (meth) acrylic acid; in an amount ranging from 0.1 to 1% by weight of active copolymer based on the total weight of the composition.

In formulations containing ASE polymers such as the copolymers described above, it is often necessary to neutralize at least a portion of the free carboxyl groups by the addition of an inorganic or organic base. Examples of suitable inorganic or organic bases include alkali metal hydroxides (e.g. sodium or potassium hydroxide), sodium carbonate, ammonium hydroxide, methylamine, diethylamine, trimethylamine, monoethanolamine, triethanolamine and mixtures thereof.

The composition of the invention may suitably include at least one inorganic electrolyte. The inorganic electrolyte may be used to help provide viscosity to the composition. The term "inorganic electrolyte" in the context of this invention denotes an inorganic salt which dissolves in water and ionizes but whose ions do not aggregate in solution as, for example, do the ions of a surface active agent which aggregate to form micelles.

Suitable inorganic electrolytes for use in the invention include metal chlorides (such as sodium chloride, potassium chloride, calcium chloride, magnesium chloride, zinc chloride, ferric chloride and aluminium chloride) and metal sulphates (such as sodium sulphate and magnesium sulphate). The inorganic electrolyte is used to assist in the solubilisation of the hydrocarbon-based oily liquid conditioning agents (ii) and to provide viscosity to the composition.

Examples of preferred inorganic electrolytes for use in the invention include sodium chloride, potassium chloride, magnesium sulphate and mixtures thereof.

Mixtures of any of the above described materials may also be suitable.

The composition of the invention may suitably have a viscosity ranging from 5,000 to 60,000 mPa·s, preferably from 5,000 to 20,000 mPa·s, more preferably from 5,000 to 15,000 mPa s, still more preferably from 5,000 to 10,000 mPa s when measured using a Brookfield LVT viscometer (spindle 3, 6 rpm, 30 seconds) at 20° C.

The pH of the final, fully-formulated composition of the invention preferably ranges from 4 to 7, more preferably from 5.5 to 6.5.

The composition of the invention may also include emulsified droplets of non-volatile silicone having a mean droplet diameter (D3,2) of 1 micrometre or less. Preferably the mean droplet diameter (D3,2) is 1 micrometre or less, more preferably 0.5 micrometre or less, and most preferably 0.25 micrometre or less.

A suitable method for measuring the mean droplet diameter (D3,2) is by laser light scattering using an instrument such as a Malvern Mastersizer.

The term "non-volatile silicone" in the context of this invention means a silicone with a vapour pressure of less than 1000 Pa at 25° C.

Suitable silicones for use in the invention include polydiorganosiloxanes, in particular polydimethylsiloxanes (dimethicones), polydimethyl siloxanes having hydroxyl end groups (dimethiconols), and amino-functional polydimethylsiloxanes (amodimethicones).

Suitable silicones preferably have a molecular weight of greater than 100,000 and more preferably a molecular weight of greater than 250,000.

All molecular weights as used herein are weight average molecular weights, unless otherwise specified.

Suitable silicones preferably have a kinematic viscosity of greater than 50,000 cS (mm$^2$·s$^{-1}$) and more preferably a kinematic viscosity of greater than 500,000 cS (mm$^2$·s$^{-1}$). Silicone kinematic viscosities in the context of this invention are measured at 25° C. and can be measured by means of a glass capillary viscometer as set out further in Dow Corning Corporate Test Method CTM004 Jul. 20, 1970.

Suitable silicones for use in the invention are available as pre-formed silicone emulsions from suppliers such as Dow Corning and GE Silicones. The use of such pre-formed silicone emulsions is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer. Pre-formed silicone emulsions having a mean droplet diameter (D3,2) of less than 0.15 micrometres are generally termed microemulsions.

Examples of suitable pre-formed silicone emulsions include emulsions DC2-1766, DC2-1784, DC-1785, DC-1786, DC-1788, DC-1310, DC-7123, DC5-7128 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Mixtures of any of the above described silicone emulsions may also be used.

When included, the amount of emulsified, non-volatile silicone in compositions of the invention may suitably range from 0.05 to 10%, preferably from 0.2 to 8% (by total weight silicone based on the total weight of the composition).

A composition of the invention may contain further optional ingredients to enhance performance and/or consumer acceptability. Examples of such ingredients include fragrance, dyes and pigments and preservatives or antimicrobials. Each of these ingredients will be present in an amount effective to accomplish its purpose. Generally these optional ingredients are included individually at a level of up to 5% by weight based on the total weight of the composition.

Mode of Use

The composition of the invention is primarily intended for topical application to the body, preferably the hair and scalp.

Most preferably the composition of the invention is topically applied to the hair and then massaged into the hair and scalp. The composition is then rinsed off the hair and scalp with water prior to drying the hair.

The invention will be further illustrated by the following, non-limiting Examples, in which all percentages quoted are by weight based on total weight unless otherwise stated.

EXAMPLES

A series of hair cleansing shampoo formulations were prepared, having ingredients as shown in Table 1 below. Examples 1 to 3 represent formulations according to the invention. Examples A to C represent comparative examples (not according to the invention).

TABLE 1

| Ingredient | Example 1 | Example 2 | Example 3 | Example A | Example B | Example C |
|---|---|---|---|---|---|---|
| | wt % (a.i.) | | | | | |
| SLES (1EO) | 14 | 14 | 14 | 14 | 14 | 14 |
| CAPB | 1.6 | 1.6 | 1.6 | 1.6 | 1.6 | 1.6 |
| DOW CORNING ® 1788 silicone emulsion | 1.3 | 1.3 | 1.3 | 1.2 | 1.2 | 1.2 |
| Sodium chloride | — | — | — | 1 | 1 | 1 |
| Zinc pyrithione (ZPT) | 0.5 | 0.5 | 0.5 | 1 | 1 | 1 |
| DOW CORNING ® 5-7128 silicone emulsion | 0.9 | 0.9 | 0.9 | 0.8 | 0.8 | 0.8 |
| Perfume | 0.8 | 0.8 | 0.8 | 0.8 | 0.8 | 0.8 |
| CARBOPOL ®980[1] | — | — | — | 0.6 | 0.6 | 0.6 |
| CARBOPOL ® Aqua SF-1[2] | 3 | 3.6 | 3 | — | — | — |
| Niacinamide | 5 | 10 | 15 | 0.5 | 1 | 2 |
| Phenoxyethanol | — | — | — | 0.5 | 0.5 | 0.5 |
| Sodium salicylate | — | — | — | 0.3 | 0.3 | 0.3 |
| DMDM hydantoin | 0.1 | 0.1 | 0.1 | — | — | — |
| Sodium hydroxide | 0.3 | 0.3 | 0.3 | 0.3 | 0.3 | 0.3 |
| Cationic guar* | 0.2 | 0.2 | 0.2 | 0.3 | 0.3 | 0.3 |

TABLE 1-continued

| Ingredient | Example 1 | Example 2 | Example 3 | Example A | Example B | Example C |
|---|---|---|---|---|---|---|
| Zinc sulphate heptahydrate | — | — | — | 0.1 | 0.1 | 0.1 |
| Water, minors | to 100 | to 100 | to 100 | to 100 | to 100 | to 100 |

*Guar hydroxypropyltrimethylammonium chloride having a DS of 0.18 and an average molecular weight ($M_w$) of about 1.35 million g/mol, from Lamberti S.p.A.
[1] Carbomer from Lubrizol, which is a homopolymer of polyacrylic acid. Carbopol ® 980 is 100% active in powder form.
[2] Acrylates Copolymer from Lubrizol, which is a crosslinked copolymer of (meth)acrylic acid with one or more C1 to C4 alkyl esters of (meth)acrylic acid. Carbopol ® Aqua SF-1 is 30% active polymer in water.

Referring to comparative examples A, B and C above, it was noted that increasing the level of niacinamide above 0.5% triggered changes in shampoo microstructure and led to a significant loss of viscosity. At 2% niacinamide (Example C) formulation viscosity could be increased to a maximum of about 4,000 mPa·s through the addition of salt. However a viscosity value of at least 5,000 mPa·s is generally considered desirable for shampoos. Raising the levels of niacinamide above 2% using the same formulation chassis as that of Examples A to C led to a system which could not be thickened at all.

By contrast, inventive Examples 1 to 3 all had viscosities of at least 10,000 mPa·s when measured using a Brookfield LVT viscometer (spindle 3, 30 seconds, 6 rpm) at 20° C. Notably, Example 3 had a measured viscosity of 10,260 mPa·s despite a niacinamide level of 15%.

TABLE 2

| Ingredient | Example D (wt %) | Example E (wt %) | Example 4 (wt %) |
|---|---|---|---|
| Sodium laureth Sulfate/SLES (1EO) | 14 | 14 | 14 |
| Cocamidopropyl Betaine | 1.6 | 1.6 | 1.6 |
| Zinc pyrithione (ZPT) | 1.0 | 1.0 | 1.0 |
| Perfume | 0.75 | 0.75 | 0.75 |
| CARBOPOL ® 980 [1] | 0.6 | — | — |
| CARBOPOL ® Aqua SF-1 [2] | — | — | 3.00 |
| CARBOPOL ® Ultrez 20^ | — | 1.00 | — |
| Niacinamide | 5 | 5 | 5 |
| Phenoxyethanol | 0.5 | 0.5 | 0.5 |
| Sodium salicylate | 0.3 | 0.3 | 0.3 |
| Sodium hydroxide | 0.25 | 0.37 | 0.13 |
| Cationic guar | 0.2 | 0.2 | 0.2 |
| Water, minors | to 100 | to 100 | to 100 |
| pH | 6 | 6 | 6 |
| Viscosity (mPa s)/Initial | 108.7 | 4102 | 7270 |
| Viscosity (mPa s)/24 hours | 121.0 | 3943 | 7308 |
| Viscosity (mPa s)/1 week | 106.5 | 3792 | 7400 |

^Actylates/C10-30 alkylacrylates crosspolymer from Lubrizol. CARBOPOL ® Ultrez 20 is 100% active.

A series of hair cleansing shampoo formulations were prepared, having ingredients as shown in Table 2 below. The cationic guar, CARBOPOL®980 and CARBOPOL® Aqua SF-1 are identical to those used in Table 1. Examples 4 represents a formulation according to the invention. Examples D and E represent comparative examples (not according to the invention).

The viscosity was measured by Discovery Hydrid Rheometer HR-2, TA instruments. For each measurement, appropriate amount of formulation was put between a lower plate of the rheometer which is a Peltier plate and an upper plate which is a Sandblasted 40 mm parallel plate. The measurement was done at 30° C., shear rate 4/s. The samples were equilibrated for 30 seconds, prior to measuring viscosity over a 30-second period. The average value of the last 15 seconds of the measurement was reported herein as the viscosity value of the sample. The viscosity obtained from this method is found equaling to the values obtained by the aforementioned Brookfield LVT viscometer.

Referring to sample D, it was noted that 5% Niacinamide leads to significant loss of viscosity, even in the presence of a structuring polymer (not according to invention). Sample E shows that another structuring polymer not according to invention may modestly increase viscosity, but the maximum is still below 5000 mPa s. The viscosity is also found decreasing over the time of storage. Example 4 contains 0.9% polymer (active) according to the invention and is stable as well as having a viscosity over 5000 mPa s.

The invention claimed is:

1. An antimicrobial personal cleansing composition comprising:
   (i) an aqueous continuous phase including one or more anionic cleansing surfactants;
   (ii) a dispersed phase including dispersed particles of zinc pyrithione (ZPT);
   (iii) a structuring polymer for the aqueous continuous phase which is selected from crosslinked alkali-swellable acrylic emulsion (ASE) polymers; and
   (iv) from 3 to 20 wt % niacinamide based on the total weight of the composition,
   wherein the structuring polymer is selected from crosslinked copolymers of (meth)acrylic acid with one or more C1 to C5 alkyl esters of (meth)acrylic acid;
   wherein the viscosity of the composition ranges from 5,000 to 20,000 mPas when measured using a Brookfield LVT viscometer (spindle 3, 6 rpm, 30 seconds) at 20° C.

2. The composition according to claim 1, wherein the anionic cleansing surfactant is sodium lauryl ether sulphate having an average degree of ethoxylation of 1, at a level of from 10 to 16% by weight based on the total weight of the composition.

3. The composition according to claim 1, wherein the level of ZPT ranges from 0.5 to 1.5% by weight based on the total weight of the composition.

4. The composition according to claim 1, which further comprises one or more cationic polymers which are selected from guar hydroxypropyltrimethylammonium chlorides having a Mw ranging from 800,000 to 2.5 million g/mol and a charge density ranging from 0.5 to 1.8 meq/g; in an amount ranging from 0.15 to 0.2% by weight based on the total weight of the composition.

5. The composition according to claim 1, wherein the amount of structuring polymer (iii) ranges from 0.1 to 1% by weight based on the total weight of the composition.

6. The composition according to claim 2, wherein the level of niacinamide ranges from 5 to 15% by weight based on the total weight of the composition.

7. The composition according to claim 2, wherein the level of ZPT ranges from 0.5 to 1.5% by weight based on the total weight of the composition.

8. The composition according to claim 2, which further comprises one or more cationic polymers which are selected from guar hydroxypropyltrimethylammonium chlorides having a Mw ranging from 800,000 to 2.5 million g/mol and a charge density ranging from 0.5 to 1.8 meq/g; in an amount ranging from 0.15 to 0.2% by weight based on the total weight of the composition.

9. The composition according to claim 2, wherein the amount of structuring polymer (iii) ranges from 0.1 to 1% by weight based on the total weight of the composition.

10. The composition according to claim 1, wherein the pH of the composition ranges from 4 to 7.

11. An antimicrobial personal cleansing composition comprising:
   (i) an aqueous continuous phase including one or more anionic cleansing surfactants;
   (ii) a dispersed phase including dispersed particles of zinc pyrithione (ZPT);
   (iii) a structuring polymer for the aqueous continuous phase which is selected from crosslinked alkali-swellable acrylic emulsion (ASE) polymers; and
   (iv) from 5 to 15 wt % niacinamide based on the total weight of the composition,
   wherein the structuring polymer is selected from crosslinked copolymers of (meth)acrylic acid with one or more C1 to C5 alkyl esters of (meth)acrylic acid;
   wherein the viscosity of the composition ranges from 5,000 to 20,000 mPas when measured using a Brookfield LVT viscometer (spindle 3, 6 rpm, 30 seconds) at 20° C.

12. The composition according to claim 1, wherein the amount of structuring polymer (iii) ranges from 3 to 3.6% by weight based on the total weight of the composition.

* * * * *